United States Patent
Sogaro

(10) Patent No.: US 8,142,402 B2
(45) Date of Patent: Mar. 27, 2012

(54) MULTICHAMBER AMPOULE FOR DISPENSING A MIXTURE CONSISTING OF SEVERAL SUBSTANCES

(75) Inventor: Alberto C. Sogaro, Kronberg (DE)

(73) Assignee: Sulzer Mixpac AG, Haag (CH)

( * ) Notice: Subject to any disclaimer, the term of this patent is extended or adjusted under 35 U.S.C. 154(b) by 32 days.

(21) Appl. No.: 12/463,494

(22) Filed: May 11, 2009

(65) Prior Publication Data

US 2009/0218241 A1    Sep. 3, 2009

Related U.S. Application Data

(63) Continuation of application No. 11/152,568, filed on Jun. 14, 2005, now Pat. No. 7,556,618.

(30) Foreign Application Priority Data

Jul. 16, 2004 (EP) .................................. 04016844

(51) Int. Cl.
*A61M 5/00* (2006.01)
(52) U.S. Cl. ...................................... 604/191
(58) Field of Classification Search .................. 604/191
See application file for complete search history.

(56) References Cited

U.S. PATENT DOCUMENTS

| 5,193,928 | A | 3/1993 | Balzer et al. | |
| 5,413,253 | A | 5/1995 | Simmen | |
| 6,135,631 | A | 10/2000 | Keller | |
| 6,161,730 | A * | 12/2000 | Heusser et al. | 222/137 |
| 6,613,021 | B2 * | 9/2003 | Sogaro | 604/191 |
| 7,367,964 | B2 | 5/2008 | Heinz et al. | |
| 7,556,618 | B2 * | 7/2009 | Sogaro | 604/191 |
| 2002/0052579 | A1 * | 5/2002 | Sogaro | 604/218 |
| 2007/0017931 | A1 * | 1/2007 | Sogaro | 222/137 |
| 2008/0203111 | A1 * | 8/2008 | Sogaro | 222/137 |

FOREIGN PATENT DOCUMENTS

| DE | 201 07 507 U | 3/2002 |
| EP | 1 426 017 A | 6/2004 |

* cited by examiner

*Primary Examiner* — Nicholas D Lucchesi
*Assistant Examiner* — Diva Ranade
(74) *Attorney, Agent, or Firm* — Quarles & Brady LLP

(57) ABSTRACT

A multichamber ampoule with a locking and dispensing mechanism to store several substances and to dispense a mixture consisting of several substances, possessing a multiple-plug closure with several plugs to selectively close and open several outlet openings in the multichamber ampoule, and an adapter for mixing the substances and dispensing the mixture, wherein the multiple-plug closure and the adapter are connected to each other in an assembly designed to be removed from the multichamber ampoule.

16 Claims, 12 Drawing Sheets

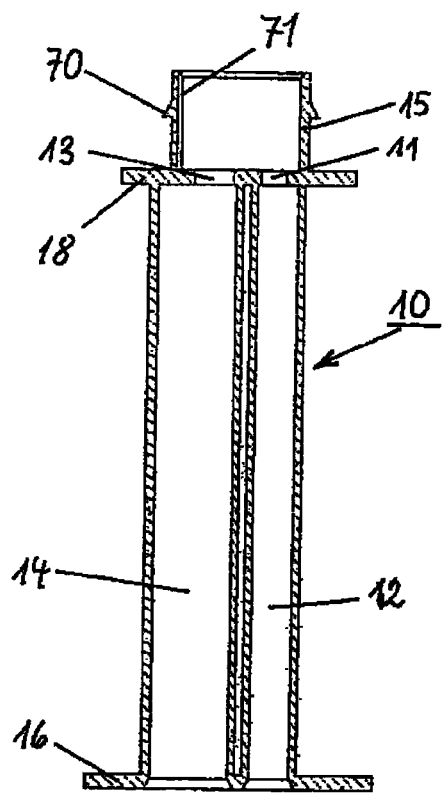
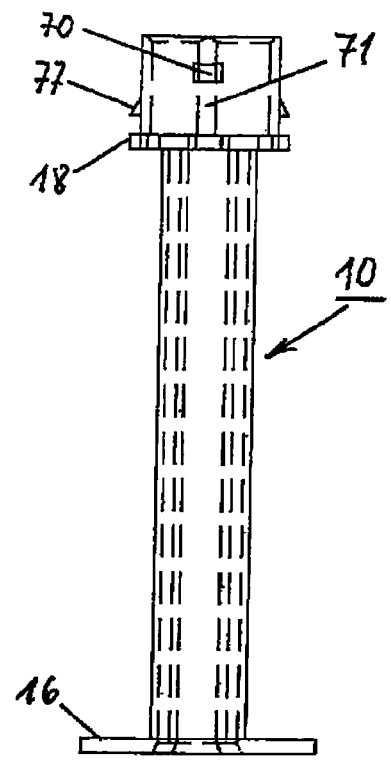
FIG. 4　　　　　　　　FIG. 5
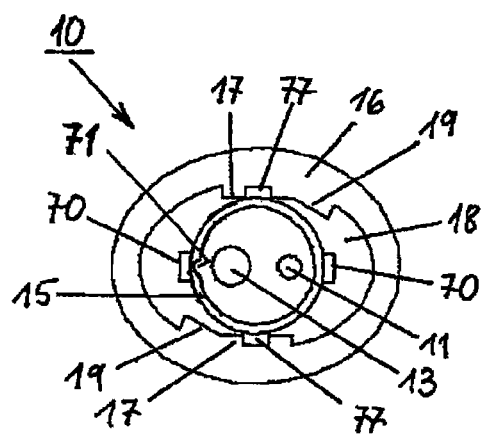
FIG. 6

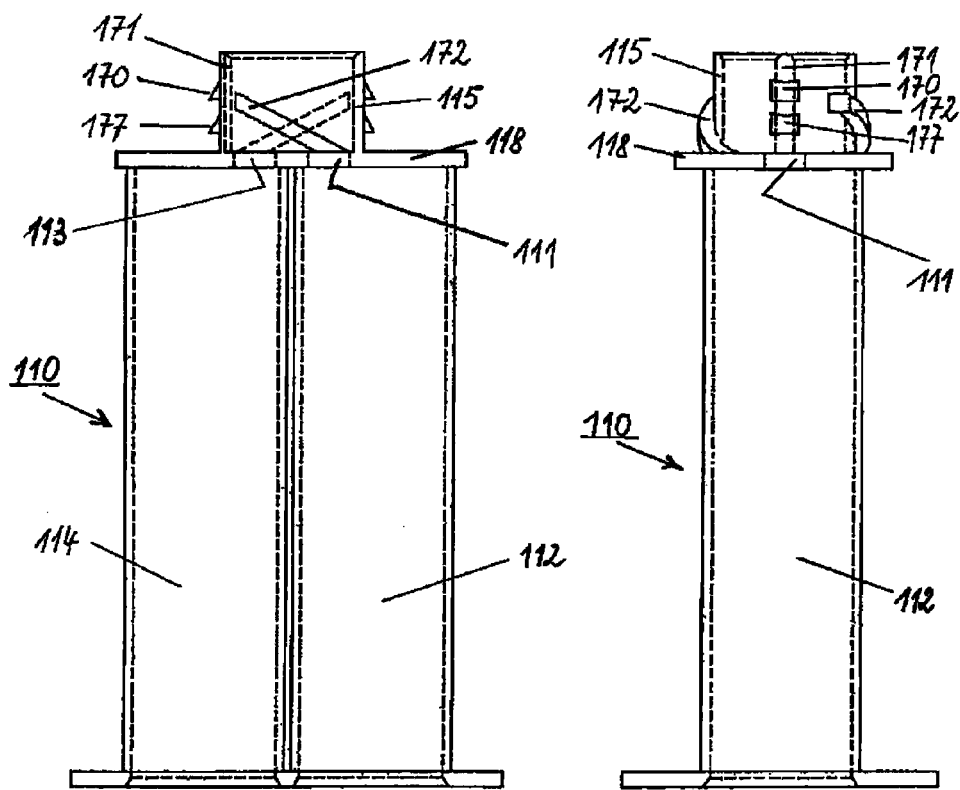
FIG. 16  FIG. 17
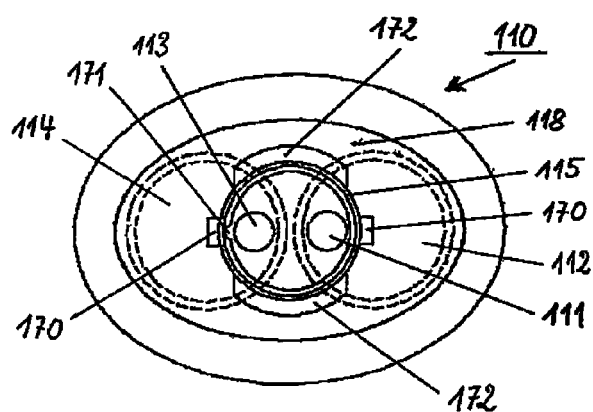
FIG.18

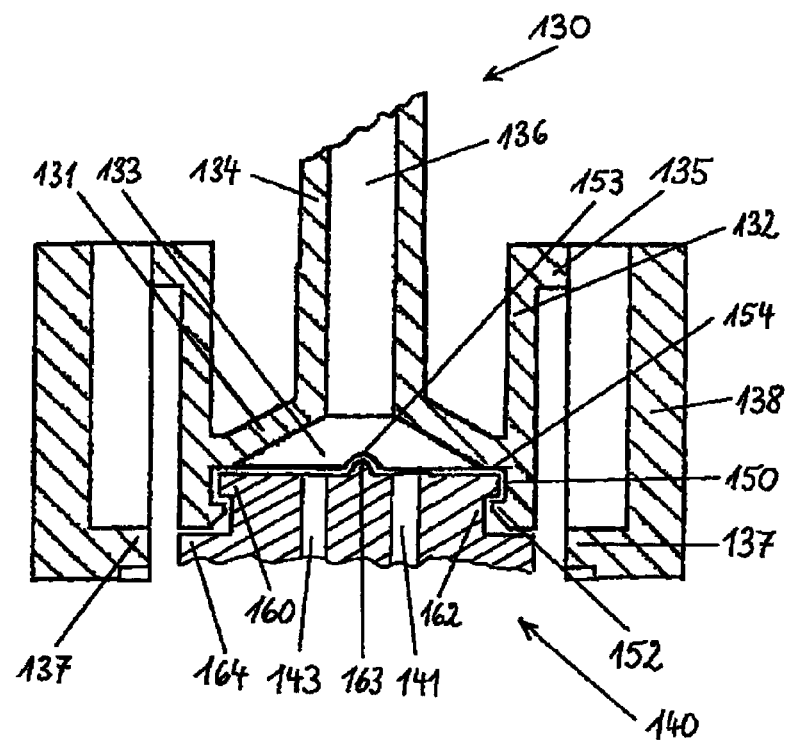
FIG. 23
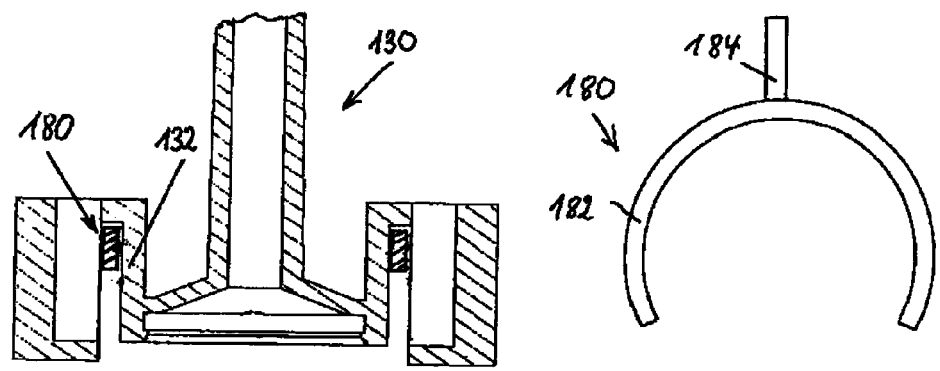
FIG. 24  FIG. 25

MULTICHAMBER AMPOULE FOR DISPENSING A MIXTURE CONSISTING OF SEVERAL SUBSTANCES

CROSS REFERENCES TO RELATED APPLICATIONS

This application is a continuation of U.S. patent Ser. No. 11/152,568 filed on Jun. 14, 2005 now U.S. Pat. No. 7,556,618, which claims the priority benefit of European Patent Application No. 04 016 844.5 filed on Jul. 16, 2004, both of which are fully incorporated herein by reference.

STATEMENT REGARDING FEDERALLY SPONSORED RESEARCH

Not Applicable.

TECHNICAL FIELD

The present invention relates to a multichamber ampoule for dispensing a mixture consisting of several substances.

DESCRIPTION OF THE BACKGROUND ART

Multichamber ampoules are known from EP 1 203 593 A1. The multichamber ampoule disclosed in EP 1 203 593 A1 was invented by the inventor of the present invention and designed as a single-use disposable article. A need exists for a multiuse multichamber ampoule.

SUMMARY OF THE INVENTION

The objective of the invention is to create a multichamber ampoule that is suitable for multiple use, easy to handle, and inexpensive to manufacture. This objective is achieved by providing a multichamber ampoule in which an adapter and multiple-plug closure can be replaced.

The invention makes it possible to separate the adapter together with the multiple-plug closure from the container of the multichamber ampoule immediately after using the multichamber ampoule, and replace it with a new adapter and multiple-plug closure assembly. An advantage of the invention is that not only can the adapter be separated from the container and discarded without requiring additional steps, but the multiple-plug closure can also be discarded. With removal of the multiple-plug closure, residual substance that was dispensed from the chambers and adhered to the closure as well as the portion still contained in the chambers can be removed. The newly assembled adapter with multiple-plug closure assembly then closes off only portions of the substances in the chambers that have not yet come in contact with each other.

The solution according to the invention provides in principle for an assembly consisting of an adapter and a multiple-plug closure for a multi-use multichamber ampoule, in which the multiple-plug closure is mounted on the adapter so as to be freely rotatable but is otherwise essentially not slidable, so that the assembly can be inserted into a container simply by manipulation of the adapter, can be removed from the container, and can be made operational in its inserted state as needed by sliding and/or rotating the adapter.

According to a preferred further development of the invention, catches are formed on the adapter and on the multiple-plug closure such that the adapter and the multiple-plug closure can interact with each other to engage in a particular rotational position. This has the advantage that when the assembly is first inserted into the container, only the rotational angle of the adapter has to be adjusted, and the multiple-plug closure automatically assumes a rotational position such that the plugs of the multiple-plug closure are aligned with the outlet openings of the chambers.

According to a further development of the invention, a radial or transverse projection is formed to project laterally from the multiple-plug closure, and a recess is formed on the container. The recess interacts with the projection such that the multiple-plug closure can only be inserted in a prescribed rotational position such that the plugs are aligned with the outlet openings of the chambers. This also facilitates the initial insertion of the assembly, particularly in combination with the above-described rotational engagement between the adapter and multiple-plug closure.

The above-described rotational alignment of the multiple-plug closure and container facilitates initial insertion, particularly when the outlet openings of the chambers and the plugs that fit into them have different cross-sectional dimensions. If a static mixer is provided in the dispensing channel of the adapter, of course the mixer will also be replaced when the adapter and multiple-plug closure assembly is replaced.

The foregoing and other objectives and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

BRIEF SUMMARY OF THE DRAWINGS

Preferred embodiments of the invention are described below using diagrams in the below described Figures, in which invisible edges are marked with broken lines in several diagrams for better visualization.

FIG. 4 shows a lateral sectional view of a container of the multichamber ampoule;

FIG. 5 shows a lateral view of the container rotated 90° in relation to FIG. 4;

FIG. 6 shows a top view of the container depicted in FIGS. 4 and 5;

FIG. 16 shows a lateral view of a container of a second embodiment of a multichamber ampoule according to the invention;

FIG. 17 shows a lateral view of the container rotated 90° in relation to FIG. 16;

FIG. 18, a top view of the container depicted in FIGS. 16 and 17;

FIG. 23 shows a lateral sectional view describing a rotational connection between adapter and multiple-plug closure;

FIG. 24 shows a lateral view of a part of the rear section of the adapter depicted in FIG. 19, and a lateral sectional view of a slidable stop piece in the form of a clip on the rear section of the adapter;

FIG. 25 shows a top view of the clip depicted in FIG. 24;

DETAILED DESCRIPTION OF THE PREFERRED EMBODIMENTS

Figure 1:
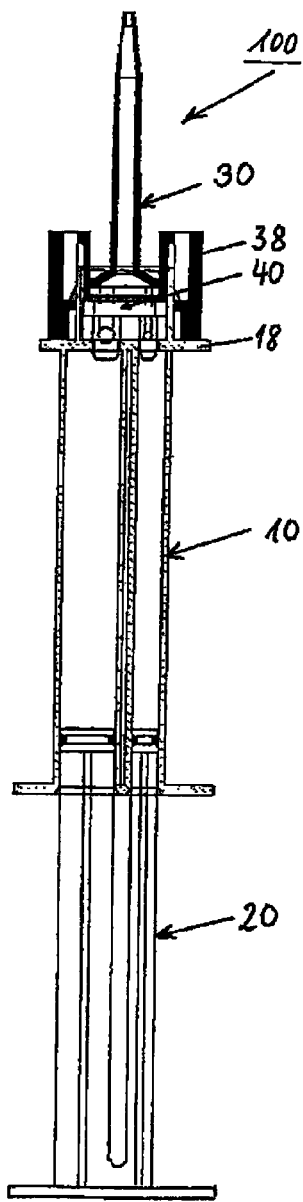
FIG. 1 shows a partial lateral sectional view of a first embodiment of a multichamber ampoule according to the invention in closed state.

A first embodiment of the invention depicted in FIGS. 1 through 15 is provided in the form of double-chamber ampoule 100. Double-chamber ampoule 100 according to the invention consists mainly of four components: container 10, plunger assembly 20, adapter 30, and multiple-plug closure 40.

As is evident in particular from FIGS. 4 through 6, container 10 has two tube-shaped chambers 12 and 14 that are arranged parallel to each other and that extend along the length of container 10. Chambers 12 and 14 are open along their entire cross-section at the back end. Back plate 18 that projects in a transverse or radial direction is formed on the external sides of the back ends of chambers 12 and 14. The front ends of chambers 12 and 14 are connected to each other by front plate 18. Outlet opening 11 for chamber 12 and outlet opening 13 for chamber 14 are provided in front plate 18. Whereas chambers 12 and 14 adjoin at the underside of the front plate 18, neck 15 is formed at the top side of front plate 18 in such a way that neck 15 surrounds outlet openings 11 and 13. Likewise to chambers 12 and 14, neck 15 extends along the length of the container 10. In the present embodiment, chamber 14 has a cross-section four times larger than chamber 12. Accordingly, the cross-section of outlet opening 13 is four times larger than that of outlet opening 11.

Figure 7:
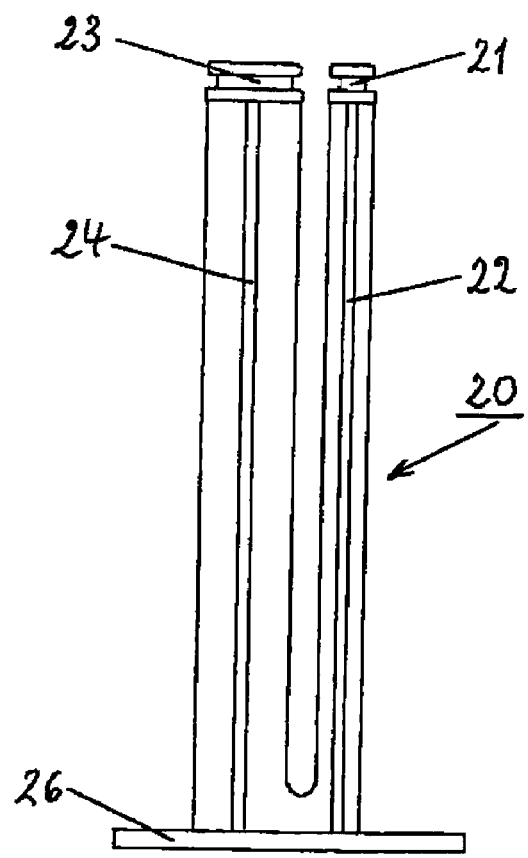
FIG. 7 shows a lateral view of a plunger assembly of the multichamber ampoule.
Figure 8:
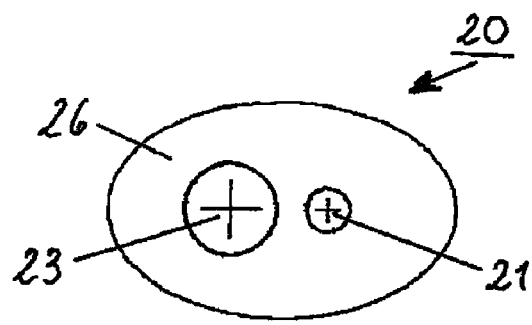
FIG. 8 shows a top view of the plunger assembly depicted in FIG. 7.
Figure 9:
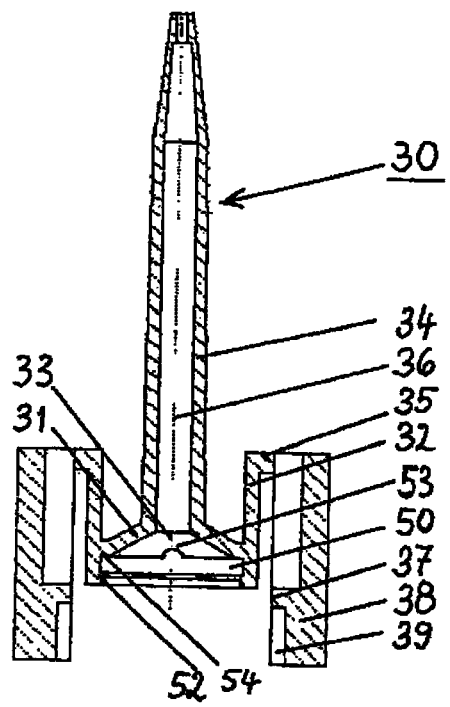
FIG. 9 shows a lateral sectional view of an adapter of the multichamber ampoule.
Figure 11:
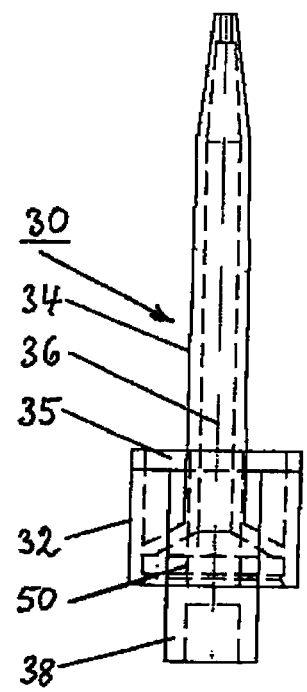
FIG. 11 shows a lateral view of the adapter rotated 90° in relation to FIG. 9.
Figure 10:
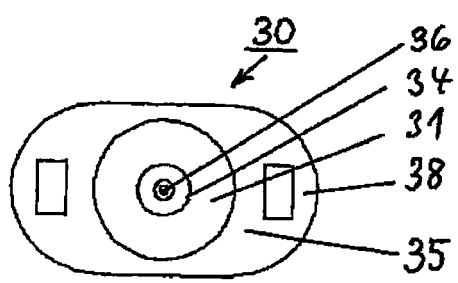
FIG. 10 shows a top view of the adapter depicted in FIG. 9.
Figure 12:
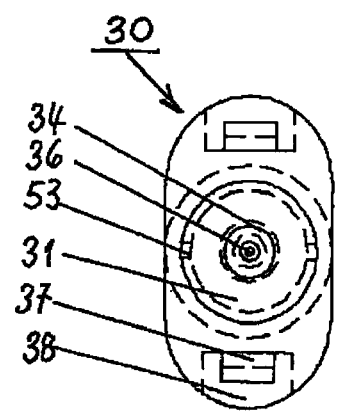
FIG. 12 shows a top view of the adapter depicted in FIG. 11.

As is evident in particular from FIGS. 7 and 8, the plunger assembly 20 comprises two plunger rods 22 and 24, whose back ends are connected by means of pressure plate 26. Plunger 21 for chamber 12 is provided at the front end of plunger rod 22. Plunger 23 for chamber 14 is provided at the front end of plunger rod 24. Plungers 21 and 23 have external cross-sectional dimensions that correspond to the internal cross-sectional dimensions of chambers 12 and 14. Plungers 21 and 23 can be inserted into the back open ends of chambers 12 and 14, and provide a fluid-tight seal when moved in chambers 12 and 14.

As is evident in particular from FIGS. 9 through 12, adapter 30, which is in the form of a dispenser piece, has cylindrical back section 32. Cylindrical back section 32 has an external diameter such that back section 32 can be inserted from above into the open front end of neck 15 and is fluid tight when pushed and rotated within it. Circumferential wall 31 that is directed inward and forward is formed along the internal surface of cylindrical back section 32 at a distance from the back end. Circumferential wall 31 borders a truncated cone-shaped mixing chamber 33 that is open at the rear. The narrower front end of circumferential wall 31 turns into a tube-shaped structure that projects beyond the front end of rear section 32, and represents front section 34 of adapter 30. Dispensing channel 36 within front section 34 extends along the length of adapter 30. The back end of dispensing channel 36 and the front end of mixing chamber 33 merge.

Transverse cross member 35 that projects radially outwards is formed at the front end of cylindrical back section 32. Locking arms 38 that project backward are formed at the underside of cross member 35, at a distance from the external circumference of the cylindrical back section 32.

Figure 13:
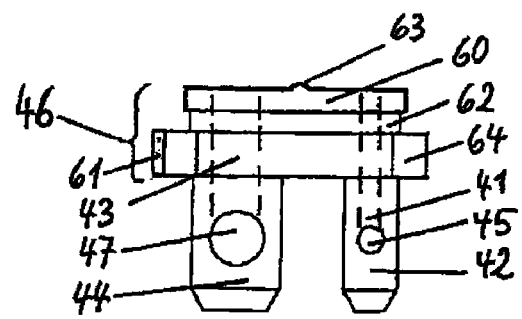
FIG. 13 shows an enlarged side view of a multiple-plug closure of the multichamber ampoule.
Figure 14:
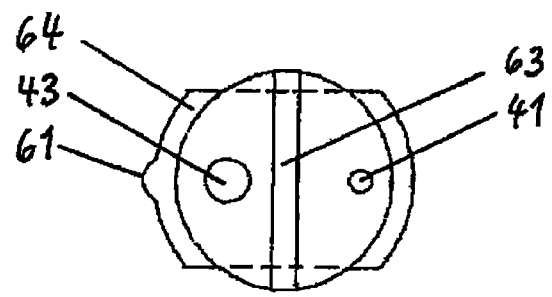
FIG. 14 shows a top view of the multiple-plug closure depicted in FIG. 13.
Figure 15:
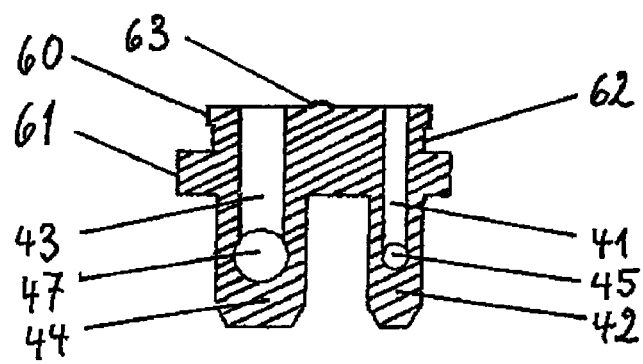
FIG. 15 shows a lateral sectional view of the multiple-plug closure depicted in FIGS. 13 and 14
Figures 19, 20:
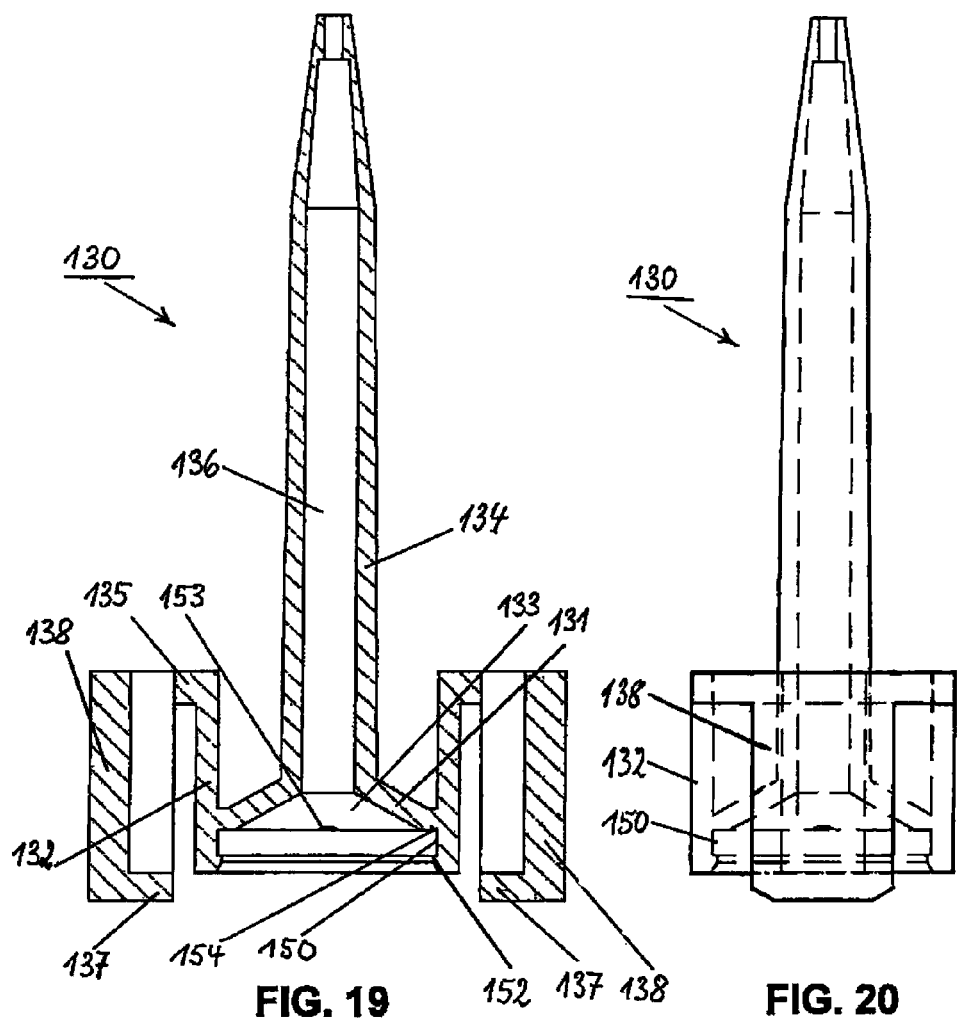
FIG. 19 shows a lateral sectional view of an adapter of the second embodiment of the multichamber ampoule.
FIG. 20 shows a lateral view of the adapter rotated 90° in relation to FIG. 19.
Figures 21, 22:
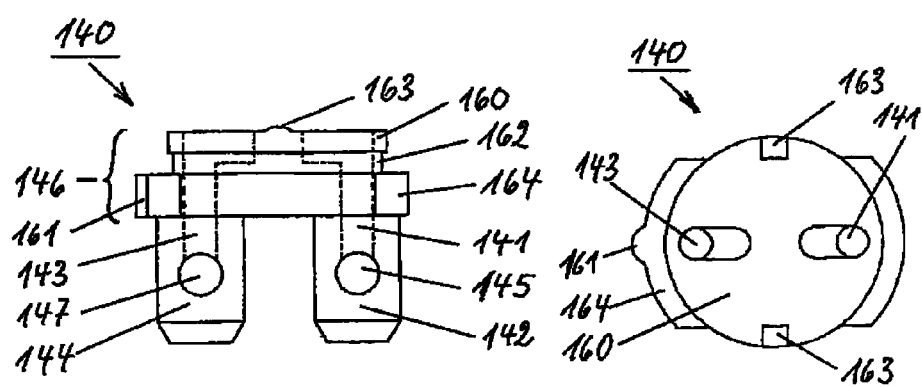
FIG. 21 shows a lateral view of a multiple-plug closure of the second embodiment of the multichamber ampoule.
FIG. 22 shows a top view of the multiple-plug closure depicted in FIG. 21.

As is evident in particular from FIGS. 13 through 15, multiple-plug closure 40 has two plugs 42 and 44 that are formed on the underside of shared plate-shaped body 46. Plate-shaped body 46 that adjoins plugs 42 and 44 comprises ground plate 64, intermediate plate 62 formed on the top side of the ground plate, and cover plate 60 that represents the front end of multiple-plug closure 40 is formed on the top side of the intermediate plate.

Two longitudinal channels 41 and 43 project downward from the top side of cover plate 60 into plugs 42 and 44. Longitudinal channel 41 joins transverse channel 45 that intersects plug 42 in a transverse direction. Longitudinal channel 43 joins transverse channel 47 that intersects plug 44 transversely. Transverse channels 45 and 47 are provided at a preset distance from the lower ends of plugs 42 and 44.

Cover plate 60 has a circular circumferential wall with a diameter that is larger than that of intermediate plate 62. To produce a rotating joint between adapter 30 and multiple-plug closure 40, cover plate 60 can be snapped from the back end of adapter 30 into ring-shaped mounting groove 50 that is provided under circumferential wall 31 on the internal surface of cylindrical back section 32 of adapter 30. The dimensions of groove 50 and cover plate 60 are coordinated in relation to each other such that cover plate 60 can rotate in groove 50. Removal of cover plate 60 from groove 50 is prevented by ring-shaped shoulder 52 that is provided at the back end of the internal surface of cylindrical back section 32. In order to facilitate snapping the cover plate into groove 50 during assembly, the surface of shoulder 52 that points radially inward is beveled as shown. Longitudinal sliding of cover plate 60 upward or forward is limited by shoulder 54 that is provided on the underside of circumferential wall 31.

Transverse rib 63 that is formed on the top side of cover plate 60 interacts with two diametrically opposed recesses 53 in shoulder 54 such that rotatable multiple-plug closure 40 mounted in adapter 30 can be engaged and released at a predetermined angular or rotational position. Adapter 30 and multiple-plug closure 40 are thus designed such that these components form a single assembly 30, 40.

When inserting the assembly consisting of adapter 30 and multiple-plug closure 40 into neck 15 of container 10 from the front or from above, plugs 42 and 44 penetrate outlet openings 11 and 13 of chambers 12 and 14. Plugs 42 and 44 are dimensioned in relation to outlet openings 11 and 13 such that the plugs in a first penetration position create a fluid-tight seal with the back end sections of outlet openings 11 and 13. Here, transverse channels 45 and 47 are located above front plate 18. The back portion of plug 44 that has penetrated outlet opening 13 has a cross-section that is four times larger than that of the back section of plug 42 that penetrates outlet opening 11.

In a further second penetration position of plugs 42 and 44 pushed further down or back, transverse channels 45 and 47 are located below front plate 18 so that a fluid connection is created above transverse channels 45 and 47 along with longitudinal channels 41 and 43 between the insides of chambers 12 and 14 and mixture chamber 33 and/or dispensing channel 36 of adapter 30. The internal cross-section of longitudinal channel 43 is four times larger than that of longitudinal channel 41. A corresponding relationship pertains to transverse channel 47 in comparison to transverse channel 45.

To better guide multiple-plug closure 40 into neck 15, ground plate 64 has a circumferential wall that fits over at least portions of the circumference of the internal circumferential wall of neck 15. Projection 61 is formed and projects radially from such a portion of the circumferential wall of the ground plate 64. Projection 61 interacts during initial insertion of multiple-plug closure 40 into neck 15 with longitudinal groove 71 that is formed along the internal surface of neck 15, such that multiple-plug closure 40 can only be inserted into neck 15 in a predetermined angular or rotational position such that plugs 42 and 44 are aligned with outlet openings 11 and 13 of chambers 12 and 14.

Locking noses 70 that project radially outward from the top side of front plate 18 are formed at a predetermined distance from the external circumferential wall of neck 15. Additional locking noses 77 that are displaced by 90° in the circumferential direction in relation to locking noses 70 and are less distant from the front plate 18 are formed on and project radially outward from the external circumferential wall of neck 15. Locking noses 77 are located above a circumferential area of front plate 18 in which recesses 17 are provided in front plate 18. Locking noses 77 project radially along recesses 17 beyond the external edge of the front plate 18, whereas locking noses 70 are provided in an unrecessed circumferential area of front plate 18, where front plate 18 projects radially beyond locking noses 70.

Locking ridges 37 that point radially inward and longitudinally running guide grooves 39 that border the underside of locking ridges 37 and run as far as the lower end of the locking arms are provided on the inside of the locking arms 38. Locking ridges 37 and guide grooves 39 interact with locking noses 70 and 77. The front surface of the lower end of locking arms 38 interacts with front plate 18. This interaction as well as the assembly and operation of double-chamber ampoule 100 will be described in the following, in particular with reference to FIGS. 1 through 3.

Figure 2:
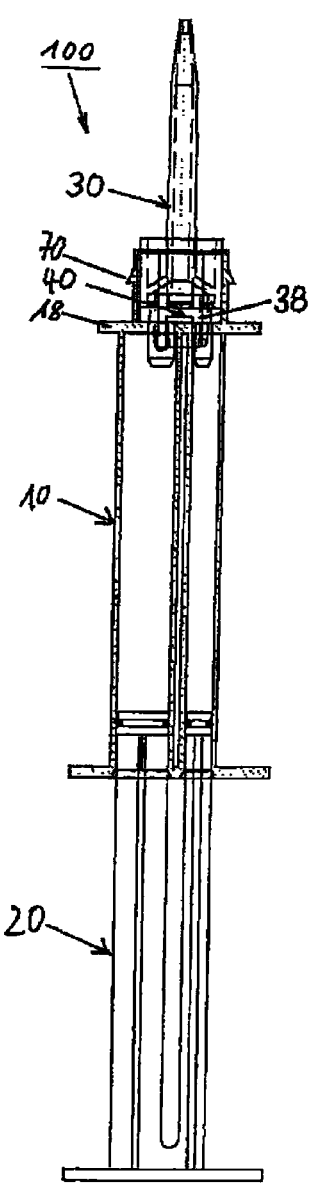
FIG. 2 shows a partial lateral view from the same perspective as in FIG. 1 of a multichamber ampoule in the activated state.
Figure 3:
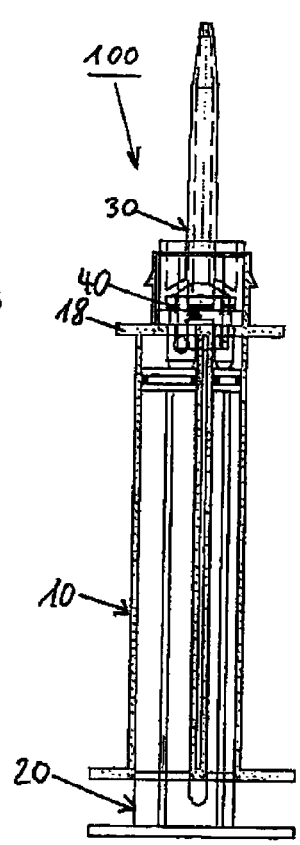
FIG. 3 shows a partial lateral sectional view of the multichamber ampoule in the emptied state from the same perspective as in FIGS. 1 and 2.

Referring to FIGS. 1 through 3, before placing the assembly consisting of adapter 30 and multiple-plug closure 40 into container 10, adapter 30 and multiple-plug closure 40 are engaged at a predetermined rotational position relative to each other, such that transverse rib 63, or locking ridge, catches locking recesses 53. Assembly 30, 40 is pushed into neck 15 of container 10 from above in this engaged state. In the process, projection 61 on multiple-plug closure 40 is aligned with longitudinal groove 71 in neck 15. In this initial rotational position of assembly 30, 40 in relation to container 10, locking arms 38 are aligned with locking noses 70. As a result, the locking noses engage guide grooves 39 when assembly 30, 40 is inserted in the initial rotational position, and plugs 42 and 44 penetrate outlet openings 11 and 13 of chambers 12 and 14. If this first rotational position of adapter 30 is pushed further in the direction of container 10, locking ridges 37 snap into locking noses 70. This prevents movement of assembly 30, 40 upward from or toward neck 15 of container 10. At the same time, continued pushing of assembly 30, 40 in the direction of container 10 is limited in this locked state in that the front surfaces at the lower end of locking arms 38 strike the top side of front plate 18. In the process, a predetermined distance is reached between plate-shaped body 46 and front plate 18, and plugs 42 and 44 penetrate just far enough into outlet openings 11 and 13 that the plugs create a fluid-tight seal with the outlet openings.

When plugs 42 and 44 are in the locked position, chambers 12 and 14 can be filled with substances through their open back ends. After being filled with substances, chambers 12 and 14 are closed from behind with plungers 21 and 23 of the plunger assembly 20. This closed position due to the plugs and the plungers is depicted in FIG. 1. The substances filling chambers 12 and 14 are not shown.

To activate double-chamber ampoule 100 that is filled with the substances, adapter 30 is rotated 90° in relation to container 10 to a second rotational position. At the beginning of rotation to the second rotational position, locking arms 38 are rotated sideways away from locking noses 70. Toward the end of the rotation, locking noses 77 spring sideways into guide grooves 39. At the same time, locking arms 38 come into alignment with recesses 17 in front plate 18. Recesses 17 in front plate 18 make it possible to push assembly 30, 40 further in the direction of container 10. In the course of this pushing, plugs 42 and 44 assume a flow position, in which transverse channels 45 and 47 are located within chambers 12 and 14. In the flow position of the plugs, locking arms 38 project downward beyond front plate 18, and locking ridges 37 snap over locking noses 77. Locking ridges 37 and locking noses 77 prevent assembly 30, 40 from being further moved forward or up from container 10 while the plugs are in the flow position. Further movement of assembly 30, 40 backward or down is prevented because the upper end of neck 15 strikes the underside of transverse cross member 35. Alternatively, further movement of assembly 30, 40 while it is in the flow position can also be prevented by the fact that plate-shaped body 46 strikes front plate 18. This activated state of double-chamber ampoule 100 is depicted in FIG. 2

By applying pressure to pressure plate 26 of plunger assembly 20, the substances contained in chambers 12 and 14 can now be expressed through the transverse and longitudinal channels of multiple-plug closure 40 into mixing chamber 33 and dispensing channel 36, and then be dispensed through the tip at front section 34 of adapter 30. For better mixing of the substances, a static mixer that is not shown is provided in the dispenser channel.

Double-chamber ampoule 100 as depicted is meant for multiple use. For this reason, only a fractional portion of the substances contained in chambers 12 and 14 is dispensed during each application. After an application is completed, adapter 30 is rotated 45° in relation to container 10 from the second rotational position to a third rotational position. This is possible because recess 17 is connected to a second recess 19, which makes rotation of the adapter from the second to the third rotational position possible. During rotation of the adapter into the third rotational position, locking arms 38 spring sideways out of locking noses 77. As a result, it is possible when in the third rotational position to pull assembly 30, 40 out of container 10 by lifting it up. As described above, a new assembly 30, 40 can then be inserted into container 10 in the initial first rotational position.

Assembly 30, 40 can be replaced multiple times by a new assembly until chambers 12 and 14 are completely empty. The empty state of multiple-chamber ampoule 100 is depicted in FIG. 3, in which case assembly 30, 40 is in the second rotational position.

A second embodiment of the invention shown in FIGS. 16 through 22 is also provided in the form of a double-chamber ampoule. Accordingly, container 110 of the second embodiment of the invention depicted in FIGS. 16 through 18 has two chambers 112 and 114 that are arranged in parallel to each other with outlet openings 111 and 113 provided for in front plate 118. In contrast to container 10 of the first embodiment, chambers 112 and 114 have the same cross-sectional dimensions. The same applies to outlet openings 111 and 113.

As with container 10, neck 115 is formed on the top side of front plate 118, into which the outlet openings 111 and 113 flow. In contrast to container 10 in the first embodiment, however, the outside of neck 115 and front plate 118 of container 110 of the second embodiment are designed differently. In other respects, container 110 and container 10 are essentially the same.

As is evident from FIGS. 16 through 18, two locking noses 170 that project radially outward and two other locking noses 177 that project radially outward are formed on the external circumferential wall of neck 115. Locking noses 170 are placed at a predetermined distance from the top side of front plate 118 and lie diametrically opposite to each other. Locking noses 177 are placed at a shorter distance from the top side of front plate 118 and also lie diametrically opposite to each other. Furthermore, in each case one of locking noses 177 is axially aligned with one of locking noses 170.

Two diagonally running ramps 172 are formed in an area of the external circumferential wall of the neck located between locking noses 170 and 177, as also is evident from FIGS. 16 through 18. Ramps 172 lie symmetrically between locking noses 170 and 177, respectively that are displaced 180° in relation to each other and enclose an angular range of approximately 90° on the cylindrical outside of neck 115. Ramps 172 have a top side that extends from one end of the ramps on the top side of front plate 118 to the other end of the ramps on the top side of front plate 118 at a predetermined distance. Viewed from the circumferential direction of neck 115, both opposing ramps 172 have the same helical sense. The function of locking noses 170 and 177 as well as of ramps 172 will be described below with reference to adapter 130 of the second embodiment of the invention depicted in FIGS. 19 and 20.

Adapter 130 differs from adapter 30 in the first embodiment largely in that locking arms 138 do not project as far down or back as in locking arms 38 in the first embodiment. Locking arms 138 end shortly or immediately behind locking ridge 137, which corresponds to locking ridge 37 of adapter 30 in the first embodiment. Furthermore, as in the first embodiment of the invention, adapter 130 is connected to multiple-plug closure 140 depicted in FIGS. 21 and 22 such that it can rotate freely. The freely rotatable connection between adapter 130 and multiple-plug closure 140 is depicted in detail in FIG. 23, which shows back section 132 of adapter 130 and a front section of multiple-plug closure 140, each in cross-section. As shown in FIG. 23, multiple-plug closure 140 has a ring-shaped cover plate 160 that is snapped into ring-shaped mounting groove 150 of adapter 130 to axially couple the multi-plug closure 140 to the adapter 130. Mounting groove 150 of adapter 130 corresponds to mounting groove 50 of adapter 30 of the first embodiment and, when viewed axially, is limited at the back end by shoulder 152 and at the front end by shoulder 154. Shoulders 152 and 154 serve as a bearing surface for cover plate 160.

Two locking noses 163 that project axially are formed on the top side of cover plate 160 in diametrically opposing positions and have the function of transverse rib 63 of cover plate 60 and interact with two diametrically opposing recesses 153 in shoulder 154 such that rotatable multiple-plug closure 140 mounted on adapter 130 can be engaged and released at a predetermined angular or rotational position. Furthermore, as with multiple-plug closure 40, multiple-plug closure 140 has two plugs 142 and 144, which, however, have the same cross-section; plate-shaped body 146, consisting of cover plate 160, intermediate plate 162, and ground plate 164; as well as two longitudinal channels 141 and 143 and two transverse channels 145 and 147. Radially projecting projection 161 is formed on the circumferential wall of ground plate 164 and interacts with longitudinal groove 171 in the inner surface of neck 115 in the same manner as described in the first embodiment of the invention. The structure and operation of the multi-chamber ampoule according to the second embodiment is explained below.

As in the first embodiment of the invention, before attaching the assembly consisting of adapter 130 and multiple-plug closure 140 to container 110, adapter 130 and multiple-plug closure 140 are engaged in a predetermined rotational position, in which locking noses 163 catch the locking recesses. In this engaged state, assembly 130, 140 is pushed into neck 115 of container 110 from above. As a result, projection 161 on multiple-plug closure 140 is aligned with longitudinal groove 171 in neck 115. In this rotational position of assembly 130, 140 in relation to container 110, locking arms 138 are aligned with locking noses 170. Because of this, when assembly 130, 140 is pushed in, locking ridges 137 strike the upper beveled section of locking noses 170, and plugs 142 and 144 begin to penetrate into outlet openings 111 and 113 of chambers 112 and 114. If in this position the adapter 130 is pushed further into container 110, locking ridges 137 snap over locking noses 170. This prevents a back movement of assembly 130, 140 up or forward out of neck 115 of the container 110. In this blocked or locked state, plugs 142 and 144 have penetrated sufficiently far into outlet openings 111 and 113 that the plugs create a fluid-tight seal with the outlet openings.

Once the above-described closed position of the plugs is achieved in which locking ridges 137 have just snapped into locking noses 170, the front surfaces of the lower end of locking arms 138 are at a distance from the top side of front plate 118. This occurs because in the second embodiment of the invention locking arms 138 are shorter than locking arms 38 in the first embodiment. However, at a suitable position between adapter 130 and container 110, a stop piece is preferably provided in the second embodiment, not shown in the Figure, which prevents continued pushing of assembly 130, 140 downward or backward in the direction of container 110 beyond the closed position of plugs 142 and 144. Such a stop piece can, for example, consist of a clip that can be torn off by hand and which is formed on adapter 130 or on container 110, and which strikes the upper side of front plate 118 of container 110 when the above-described closed position of plugs 142 and 144 is reached.

As in the first embodiment of the invention when plugs 142 and 144 are in the closed position, chambers 112 and 114 can be filled with substances through their open back end and then closed off with plungers. To activate a double-chamber ampoule that is filled with substances according to the second embodiment, the above-mentioned stop piece is removed, and the adapter and multiple-plug closure assembly 130, 140 are pushed further backward in the direction of container 110. In the course of this movement, locking ridges 137 snap over locking noses 177, while at the same time plugs 142 and 144 assume the flow position. Locking ridges 137 that snap over locking noses 177 prevent assembly 130, 140 from being pushed forward or up from container 110 while in the flow position. Pushing assembly 130, 140 further back or down is prevented because the front surfaces of the lower end of locking arms 138 strike the top side of front plate 118.

With regard to the above-mentioned stop piece, FIGS. 24 and 25 show an embodiment of slidable clip 180 on cylindrical back section 132 of adapter 130. Clip 180 consists of open ring-shaped section 182, which, for example, extends over 270°, and pull tab 184 that is formed at a position diametrically opposite the opening in ring-shaped section 182 on the outside of ring-shaped section 182 in the manner shown. When slid open, clip 180 strikes the top side of neck 115 of container 110, and in this manner prevents adapter 130 from being pushed beyond the closed position when the multichamber ampoule is activated. Clip 180 is pulled off of back section 132 by grabbing hold of pull tab 184 before activating the multichamber ampoule.

With the clip 180 pulled off of back section 132, the double-chamber ampoule according to the second embodiment of the invention is now in the activated state. In the activated state, pressure exerted on the plungers in chambers 112 and 114 dispenses the substances contained in the chambers through the transverse and longitudinal channels of multiple-plug closure 140 into mixing chamber 133 of adapter 130. The substances are dispensed in a mixed state out through the front tip of adapter 130.

The double-chamber ampoule according to the second embodiment of the invention is envisioned for either single use or multiple use, just like double-chamber ampoule 100 according to the first embodiment. In multiple use, only a fractional portion of the substances stored in chambers 112 and 114 are dispensed during any single application. After an application is completed, adapter 130 is rotated out of its original inserted position in container 110. When adapter 130 is rotated, locking arms 138 spring sideways out of locking noses 177, and the front surfaces of the lower ends of locking arms 138 reach ramps 172 that run diagonally upward or forward.

In the course of rotating adapter 130 further in relation to container 110, adapter 130 is pushed away upward or forward from container 110 by ramps 172. In the process, multiple-plug closure 140 that is connected with adapter 130 such that it can rotate is also pulled forward or upward. The gradient of ramps 172 is calculated such that before reaching the foremost end of the ramp, plugs 142 and 144 have been almost completely pulled out of outlet openings 111 and 113. Assembly 130, 140 can then be removed from neck 115 of container 110 without effort. A new assembly 130, 140 can then be inserted into container 110.

It should be mentioned that the multichamber ampoule according to the invention can either be applied directly by hand by using the plunger assembly shown in FIGS. 7 and 8, or by using a known dispensing gun. When using a dispensing gun, the plunger rods including pressure plate shown in FIGS. 7 and 8 are omitted. In that case, plungers in the form of plugs that are directly activated by the output gun are used in the container chambers.

In order to enable snap closure between locking arms 38, 138 of adapter 30, 130 and locking noses 70, 77, 170, 177 as well as releasable engagement between transverse rib 63 or locking noses 163 and locking recesses 53, 153, the interacting portions of the components must be manufactured out of a material that allows for a certain elasticity. Thermoplastics such as polyethylene, polyethylene terephthalate, polypropylene, cycloolefin copolymers, and the like, that are processable by compression molding or injection molding are preferred for manufacturing the parts of the multichamber ampoule according to the invention.

The above-described embodiments of the invention should not be viewed as limitations on the invention. Rather, one skilled in the art can make changes and alterations that are still within the scope of the invention. Thus, for example, the ramps can enclose an angular range other than 90°. Moreover, for example, instead of a ramp on the neck of the container, a bevel can be formed on the adapter or on both the adapter and the container. At the same time, the specified engaging and locking mechanisms can be varied in various ways while serving the same function.

With regard to the above-cited bevels on the adapter and/or containers, see FIGS. 26 through 33. The same reference numbers are used in FIGS. 26 through 33 to represent what are essentially the same components as in FIGS. 1 through 15. Altered or additional characteristics are identified with additional reference numbers. In addition, for the sake of clarity only container 10 and the adapter 30 are depicted in FIGS. 26 through 33.

FIGS. 26 through 29 serve to explain a first further development of the first embodiment of the invention. As is evident from FIGS. 26 and 28, bevel 274 is provided on the lower or rear end of locking arm 38. As is evident from FIGS. 27 and 29, recess 19 has been omitted from front plate 18 of container 10.

Figure 26:
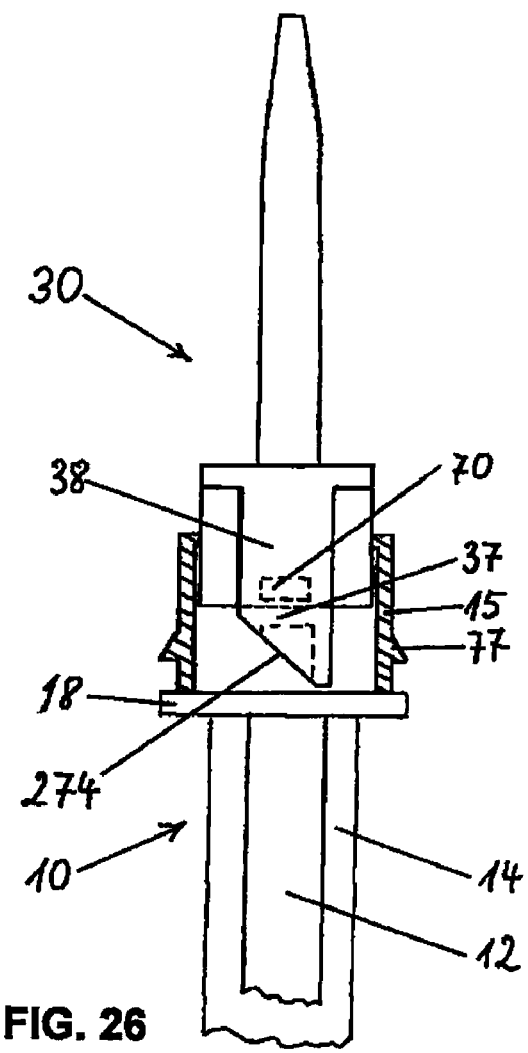
FIG. 26 shows a partial lateral sectional view of the adapter and container of a first further development of the first embodiment in the closed state.
Figure 27:
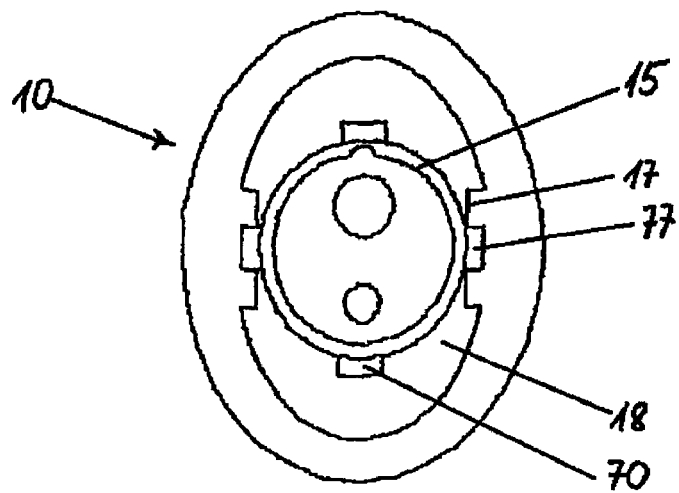
FIG. 27 shows a top view of the container depicted in FIG. 26.

FIG. 26 shows the position between adapter 30 and container 10 in the closed position. Here, locking ridge 37 is snapped in behind locking nose 70, and the lowest or hindmost end of locking arm 38 that is not touched by bevel 274 strikes front plate 18 of the container in order to prevent movement while in the activated position.

Figure 28:
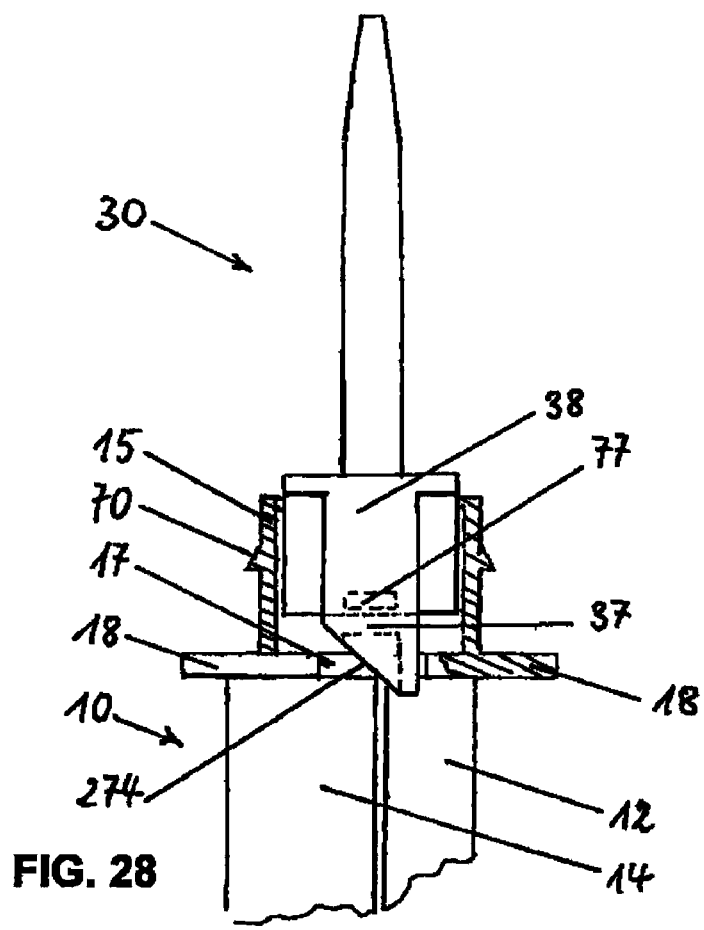
FIG. 28 shows a partial lateral sectional view of the adapter and container of the first development of the first embodiment depicted in FIG. 26 in the activated state.
Figure 29:
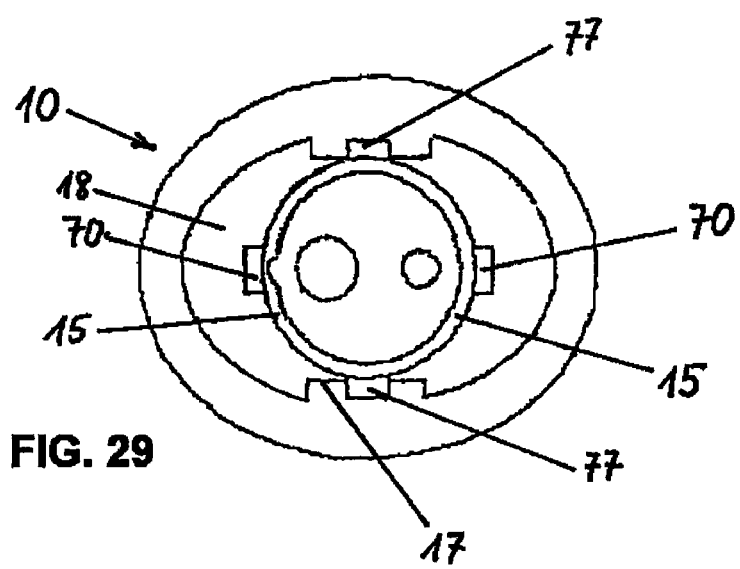
FIG. 29 shows a top view of the container depicted in FIG. 28.

To activate, adapter 30 is rotated 90° as in the first embodiment of the invention, and then pushed downward or backward until locking ridge 37 snaps over locking nose 77. To remove adapter 30 and multiple-plug closure 40, which is not depicted, adapter 30 is rotated further in the same direction. Because of the distance between bevel 274 and the edge of recess 17, which is shown in FIG. 28, this continued rotation of adapter 30 ends in the unlocked state. Subsequently, bevel 274 catches recess 17 and pushes adapter 30 together with multiple-plug closure 40, which is not depicted, up and out of neck 15 of container 10.

FIGS. 30 through 33 serve to explain a second development of the first embodiment of the invention. As is evident from FIGS. 30 and 32, rectangular recess 376 is provided in the right half of the lower section of locking arm 38 shown in the diagram, which extends at most to the lower side of locking ridge 37. The left half of the section of locking ridge 37 shown in the diagram is in the form of bevel 374 as indicated.

Figure 30:
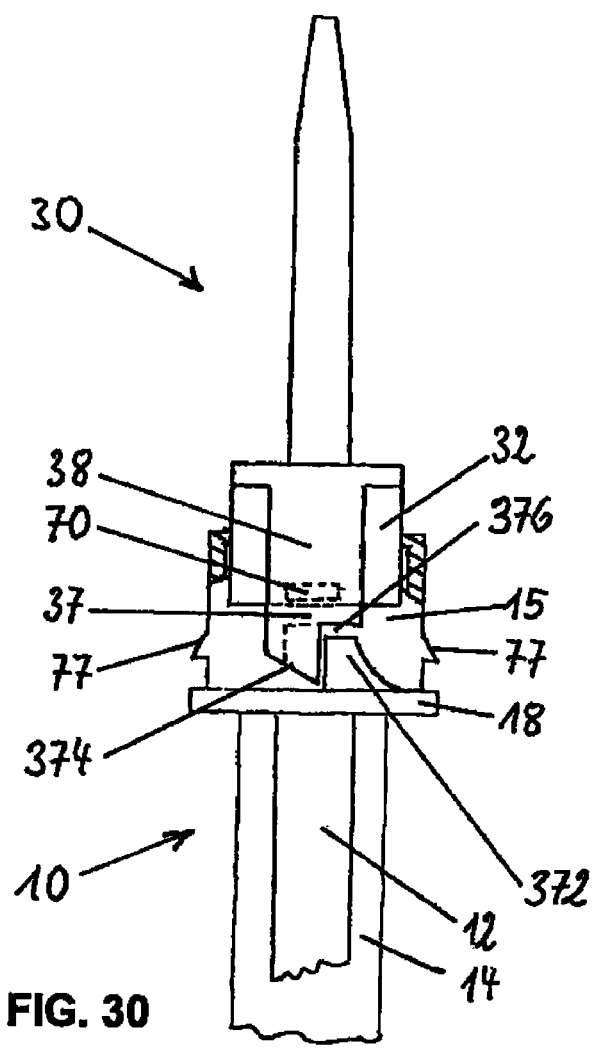
FIG. 30 shows a partial lateral sectional view of the adapter and container of a second development of the first embodiment in the closed state.
Figure 31:
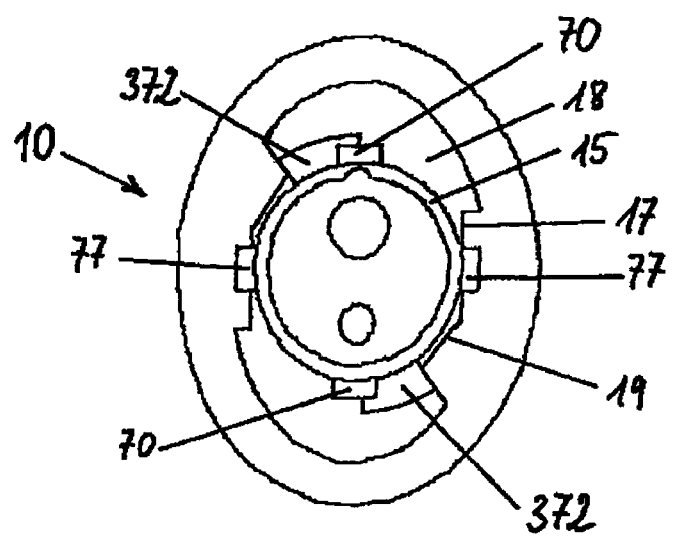
FIG. 31 shows a top view of the container depicted in FIG. 26.

As is evident from FIGS. 30 through 33, two diametrically opposed ramps 372 are formed on the top side of front plate 18. FIG. 30 shows the relationship between container 10 and adapter 30 when the multichamber ampoule is in the closed state. Here, locking ridge 37 is snapped in behind locking nose 70. Pushing adapter 30 downward or backward beyond the closed position is prevented by the fact that the lowest or hindmost end of bevel 374 strikes the top side of front plate 18 and/or the upper edge of recess 376 at the top side of ramp 372. Ramp 372 is shaped in such a way that it is at its greatest distance from the top side of front plate 18 where it is at locking nose 70, and this decreases from there in the direction of recess 19 until it reaches the level of front plate 18.

Figure 32:
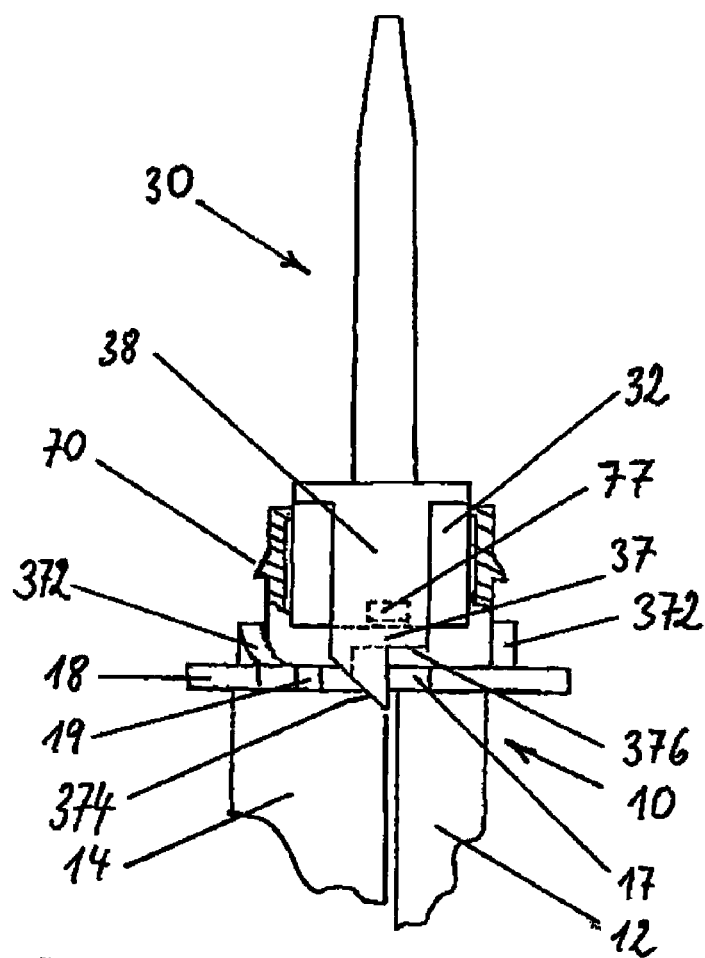
FIG. 32 shows a partial lateral sectional view of the adapter and container of the second development of the first embodiment depicted in FIG. 26 in the activated state.
Figure 33:
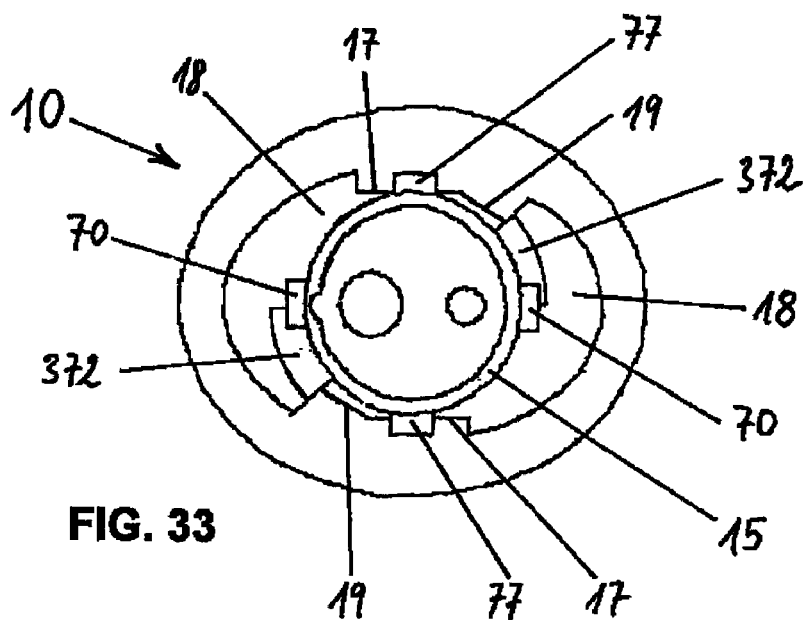
FIG. 33 shows a top view of the container depicted in FIG. 32.

In order to activate the multichamber ampoule in the first development of the first embodiment of the invention, adapter 30 is rotated by 90° in relation to container 10 and is then pushed down into the position shown in FIG. 32. In this connection, it should be noted that when rotating from the closed position depicted in FIG. 30, the end located at locking nose 70 represents a catch that allows rotation in only one direction. In the example depicted, the direction of rotation is to the right.

To remove adapter 30, including multiple-plug closure 40, which is not depicted, adapter 30 is rotated further to the right and out of the position shown in FIG. 32. Because of the distance between the edge of recess 19 and bevel 374, the adapter first assumes the unlocked position. When then rotated to the right, bevel 374 runs up the edge of recess 19 and reaches the top side of ramp 372. The dimensions of ramp 372 and of the bevel are such that when rotation of adapter 30 out of the activated position is continued, locking arm 38 is pushed up so far that before reaching locking nose 70, locking ridge 37 is lifted over locking nose 70 so that accidental locking is avoided when removing adapter 30.

While there has been shown and described what are at present considered the preferred embodiments of the invention, it will be obvious to those skilled in the art that various changes and modifications can be made therein without departing from the scope of the invention defined by the appended claims.

I claim:

1. A multichamber ampoule to dispense a mixture consisting of several substances, said ampoule comprising:
a container having at least two chambers, each of said chambers having back end and a front end, said back end being open to feed in one of the substances and subsequently insert a plunger into the chamber, and said front end having an outlet opening;
a hollow cylindrical neck formed at the front ends of said chambers into which outlet openings of the chambers feed;
a multiple-plug closure inserted into the neck, said multiple plug closure having a body with at least two plugs, each of said plugs extending toward the outlet opening of one of the chambers, said multiple-plug closure being movable between a first position and a second position, in said first position, said plugs extend into the outlet openings forming substantially fluid-tight seals with said outlet openings, and in said second position said plugs allow fluid to pass through the outlet openings;
an adapter having a back section received in the neck and coupled to said multiple-plug closure, said adapter being movable in said neck to move said multi-plug closure between said first position and said second position, wherein moving said adapter toward said chambers causes said multiple-plug closure to move between said first position and said second position; and,
a locking mechanism formed on the container and adapter, said locking mechanism resisting movement of the adapter from causing the multiple-plug closure to move from the first position to the second position once the multiple-plug closure is in the first position;
wherein the body of the multiple-plug closure is coupled to the back section of the adapter such that the adapter can be rotated relative to the multiple-plug closure, and the locking mechanism is formed such that the adapter can be rotated from the first position toward the second position relative to the multiple-plug closure that is not rotatable in the outlet openings of the chambers, in the second position the adapter is removable from the neck of the container together with the multiple-plug closure and is separable from the container.

2. The multichamber ampoule according to claim 1, in which a bevel is formed on the container and/or on the adapter, which when the adapter is rotated toward the second position, said bevel urges the adapter together with the multiple-plug closure away from the container.

3. The multichamber ampoule according to claim 2, in which a ramp is formed on the neck of the container.

4. The multichamber ampoule according to claim 1, in which a stop piece is provided between the container and the adapter, which interacts such that when the adapter is first inserted into the container, a backward movement of the multiple-plug closure that is caused by the adapter is limited from going beyond the first position.

5. The multichamber ampoule according to claim 4, in which the stop piece possesses a removable pull tab formed on the container and/or on the adapter, which after its removal allows the adapter to be move toward the container urging the multiple-plug closure from the first position toward the second.

6. The multichamber ampoule according to claim 1, in which other locking mechanisms are formed on the adapter and container, which, when the adapter is initially inserted into the container, interact such that they prevent the adapter from being moved away from said chambers once said multiple-plug closure reaches the first position.

7. The multichamber ampoule according to claim 1, in which the container has a front plate that extends at a right angle to a longitudinal axis of the chambers, said front plate being formed with a bottom plate surface on the front ends of the chambers, and in which the outlet openings of the chambers are formed, and the container neck possesses an open front end and a back end formed on an upper plate surface of the front plate, which surround the outlet openings of the chambers that are provided in the front plate.

8. The multichamber ampoule according to claim 1, in which a transverse cross member is formed on the adapter onto which are formed locking arms that project toward said container and parallel to an external circumferential wall of the container neck when the back section of the adapter is inserted into the neck of the container, and in which locking noses that are formed on the external circumferential wall of the container neck interact with the locking arms.

9. The multichamber ampoule according to claim 7, in which during rotation of the adapter, lower front surfaces of the locking arms run up a ramp.

10. The multichamber ampoule according to claim 4, in which the front plate of the container extends radially beyond the external circumferential wall of the container neck, and in which when first inserting the adapter into the container in a first rotational position between the adapter and the container, the locking arms strike an upper plate surface of the front plate when the first position is reached by the multiple-plug closure when movement of the multiple-plug closure is effected by the adapter.

11. The multichamber ampoule according to claim 5, in which the adapter can be rotated out of the first rotational position into a second rotational position, in which the locking arms of the adapter are provided with recesses in the front plate so that the adapter can be pushed further toward the container while in the second rotational position, in which the locking arms project past the front plate of the container and prevent further movement of the adapter away from the container once the multiple-plug closure has assumed the second position of the multiple-plug closure as a result of movement effected by the adapter.

12. The multichamber ampoule according to claim 6, in which the recesses in the front plate extend over an angular range from the second rotational position to a third rotational position, so that the adapter in the second rotational position can be rotated out of the second rotational position and into the third rotational position, in which the adapter can be removed along with the multiple-plug closure by pulling the adapter away from the container.

13. The multichamber ampoule according to claim 1, in which a catch is formed on the back section of the adapter and on the body of the multiple-plug closure, which interact such that the adapter and the multiple-plug closure can be engaged with each other in a predetermined rotational angle position.

14. The multichamber ampoule according claim 1, in which a projection that projects out at a right angle is formed on the body of the multiple-plug closure, and which interacts with a longitudinal groove on an inside of the neck in such a way that the multiple-plug closure can only be inserted in a predetermined rotational angular position into the container neck, and in which the plugs of the multiple-plug closure are aligned with the outlet openings of the chambers allocated to them.

15. The multichamber ampoule according to claim 1, in which the chambers have different cross-sectional dimensions; and in which the plunger, the outlet openings, and the plugs have dimensions that fit to them.

16. A locking and dispensing mechanism for a multichamber ampoule to store several substances and to dispense a mixture consisting of several substances, said mechanism comprising:
   a multiple-plug closure with several plugs to selectively close and open several outlet openings in the multichamber ampoule; and
   an adapter to mix the substances and dispense the mixture, wherein the multiple-plug closure and the adapter are rotatably connected to each other in an assembly designed to be removed from the multichamber ampoule.

* * * * *